US012249425B2

(12) United States Patent
Shvets et al.

(10) Patent No.: US 12,249,425 B2
(45) Date of Patent: Mar. 11, 2025

(54) INSULIN TITRATION ALGORITHM BASED ON PATIENT PROFILE

(71) Applicant: Novo Nordisk A/S, Bagsvaerd (DK)

(72) Inventors: Oleksandr Shvets, Yardley, PA (US); Tinna Bjoerk Aradottir, Copenhagen (DK); Thomas Dedenroth Miller, Seattle, WA (US); Anuar Imanbayev, Seattle, WA (US)

(73) Assignee: Novo Nordisk A/S, Bagsvaerd (DK)

( * ) Notice: Subject to any disclaimer, the term of this patent is extended or adjusted under 35 U.S.C. 154(b) by 482 days.

(21) Appl. No.: 16/622,384

(22) PCT Filed: Jun. 14, 2018

(86) PCT No.: PCT/EP2018/065845
§ 371 (c)(1),
(2) Date: Dec. 13, 2019

(87) PCT Pub. No.: WO2018/229209
PCT Pub. Date: Dec. 20, 2018

(65) Prior Publication Data
US 2020/0227170 A1    Jul. 16, 2020

Related U.S. Application Data

(60) Provisional application No. 62/522,811, filed on Jun. 21, 2017, provisional application No. 62/520,139, filed on Jun. 15, 2017.

(30) Foreign Application Priority Data

Jun. 29, 2017   (EP) ..................... 17178877

(51) Int. Cl.
*G16H 50/50* (2018.01)
*A61B 5/00* (2006.01)
(Continued)

(52) U.S. Cl.
CPC ........... *G16H 50/30* (2018.01); *A61B 5/4839* (2013.01); *A61B 5/4848* (2013.01);
(Continued)

(58) Field of Classification Search
CPC ........ G16H 50/30; G16H 50/50; G16H 20/17; A61B 5/4839; A61B 5/4848;
(Continued)

(56) References Cited

U.S. PATENT DOCUMENTS 6,573,679 B1   6/2003   Villaret
6,923,763 B1   8/2005   Kovatchev et al.
(Continued)

FOREIGN PATENT DOCUMENTS

CA    2547224 A1    11/2006
CN    102264283 A    11/2011
(Continued)

OTHER PUBLICATIONS

Khashei et al "A Novel Hybrid Classification Model of Artificial Neural Networks and Multiple Linear Regression Models", Expert Systems with Applications, 2012. pp. 2606-2620. https://www.sciencedirect.com/science/article/pii/S0957417411012474. Accessed Jan. 28, 2022. (Year: 2012).*
(Continued)

*Primary Examiner* — Stella Higgs
*Assistant Examiner* — Aaisha Abdullah
(74) *Attorney, Agent, or Firm* — Wesley Nicolas

(57) ABSTRACT

A device, system and method is provided for predicting risk of hypoglycemia and adjusting an insulin medicament dose size for a subject being on pen based multi-daily injections. A first algorithm is provided for computing a first insulin dose size based on a plurality of timestamped blood glucose (BG) measurements and insulin injected dose sizes. A risk prediction module is adapted to, based on machine learning
(Continued)

algorithms, predict risk of hypoglycemia based on the time-stamped BG measurements and calculate a second insulin dose size resulting in a non-hypoglycemic state. In case the second dose size is lower than the first dose size, the first dose size is automatically adjusted down to the second dose size and communicated as the recommended dose size to the subject.

4 Claims, 5 Drawing Sheets

(51) Int. Cl.
- *G16H 10/60* (2018.01)
- *G16H 20/17* (2018.01)
- *G16H 50/20* (2018.01)
- *G16H 50/30* (2018.01)
- *G16H 70/20* (2018.01)
- *G16H 70/40* (2018.01)
- *G16H 70/60* (2018.01)
- *A61B 5/145* (2006.01)
- *A61M 5/178* (2006.01)

(52) U.S. Cl.
CPC .......... *A61B 5/7267* (2013.01); *A61B 5/7275* (2013.01); *G16H 10/60* (2018.01); *G16H 20/17* (2018.01); *G16H 50/20* (2018.01); *G16H 50/50* (2018.01); *G16H 70/20* (2018.01); *G16H 70/40* (2018.01); *G16H 70/60* (2018.01); *A61B 5/14532* (2013.01); *A61M 5/178* (2013.01); *A61M 2205/3584* (2013.01); *A61M 2205/3592* (2013.01)

(58) Field of Classification Search
CPC . A61B 5/7267; A61B 5/7275; A61B 5/14532; A61M 5/178; A61M 2205/3584; A61M 2205/3592
See application file for complete search history.

(56) References Cited

U.S. PATENT DOCUMENTS

| | | | |
|---|---|---|---|
| 8,370,077 B2 | 2/2013 | Bashan et al. | |
| 8,562,587 B2 | 10/2013 | Kovatchev et al. | |
| 8,688,386 B2 | 4/2014 | Shadforth et al. | |
| 10,046,113 B2 | 8/2018 | Ruchti et al. | |
| 10,255,992 B2 | 4/2019 | Booth et al. | |
| 10,272,198 B2 | 4/2019 | Bashan et al. | |
| 10,478,100 B2 | 11/2019 | Tubb | |
| 10,617,363 B2 | 4/2020 | Diebold et al. | |
| 10,842,419 B2 | 11/2020 | Kovarchev et al. | |
| 11,147,920 B2 * | 10/2021 | Finan | A61M 5/14244 |
| 2005/0065760 A1 | 3/2005 | Murtfeldt et al. | |
| 2005/0192494 A1 * | 9/2005 | Ginsberg | G16H 20/17 600/365 |
| 2007/0092888 A1 * | 4/2007 | Diamond | C12Q 1/6883 702/20 |
| 2009/0304665 A1 | 12/2009 | Frost et al. | |
| 2009/0326357 A1 * | 12/2009 | Weinert | G16H 20/17 600/365 |
| 2010/0075353 A1 | 3/2010 | Heaton | |
| 2010/0162786 A1 | 7/2010 | Keenan et al. | |
| 2010/0256047 A1 | 10/2010 | Sieh et al. | |
| 2011/0119212 A1 * | 5/2011 | De Bruin | A61B 5/00 706/12 |
| 2011/0313674 A1 | 12/2011 | Duke et al. | |
| 2011/0319322 A1 | 12/2011 | Bashan et al. | |
| 2012/0172694 A1 * | 7/2012 | Desborough | A61B 5/7275 600/365 |
| 2012/0232520 A1 | 9/2012 | Sloan et al. | |
| 2012/0253840 A1 * | 10/2012 | Murata | G16H 10/40 705/2 |
| 2013/0179184 A1 | 7/2013 | Hurst | |
| 2014/0221966 A1 * | 8/2014 | Buckingham | A61M 5/14244 604/504 |
| 2014/0350369 A1 | 11/2014 | Budiman et al. | |
| 2015/0006456 A1 * | 1/2015 | Sudharsan | G16H 40/63 706/46 |
| 2015/0190098 A1 * | 7/2015 | Patek | A61B 5/7278 600/365 |
| 2015/0273147 A1 * | 10/2015 | Duke | A61B 5/14532 703/2 |
| 2017/0068790 A1 | 3/2017 | Fuerst | |
| 2017/0091419 A1 * | 3/2017 | Hoglund | G16H 20/13 |
| 2017/0252514 A1 * | 9/2017 | Duke | A61M 5/1723 |
| 2017/0332952 A1 * | 11/2017 | Desborough | A61M 5/14276 |
| 2017/0358200 A1 * | 12/2017 | Newman | A61B 5/746 |
| 2018/0207484 A1 * | 7/2018 | Briggs | G16H 50/70 |
| 2019/0287645 A1 * | 9/2019 | Abdueva | G16B 30/10 |

FOREIGN PATENT DOCUMENTS

| | | | | |
|---|---|---|---|---|
| CN | 102369032 A | 3/2012 | | |
| CN | 103400028 A | 11/2013 | | |
| CN | 107809943 A | 3/2018 | | |
| JP | 2002531885 A | 9/2002 | | |
| JP | 2005326943 A | 11/2005 | | |
| JP | 2012518498 A | 8/2012 | | |
| JP | 2016517601 A | 6/2016 | | |
| JP | 2017505696 A | 2/2017 | | |
| TW | 201333870 A | 8/2013 | | |
| WO | WO-2008143943 A1 * | 11/2008 | | A61B 5/0004 |
| WO | 2009/048462 A1 | 4/2009 | | |
| WO | 2011157402 A1 | 12/2011 | | |
| WO | 2014145049 A2 | 9/2014 | | |
| WO | 2015169814 A1 | 11/2015 | | |

OTHER PUBLICATIONS

Howard Zisser et al., "Bolus Calculator: A Review of Four "Smart" Insulin Pumps," Diabetes Technology & Therapeutics. 2008, vol. 10, No. 6, pp. 441-444.
Sabine Arnolds, M.D. et al, "Common Standards of Basal Insulin Titration in T2DM," J Diabetes Sci Technol, 2013, vol. 7, No. 3, pp. 771-788.
S. Wolfe, "Contribution of the dawn phenomenon to the fasting and postbreakfast hyperglycaemia in type 1 diabetes treated with once-nightly insulin glargine", Endocr Pract., 2012, vol. 18, pp. 558-562.
T. Walker, "The Rationale for Continous Glucose Monitoring-based Diabetes Treatment Decisions and Non-adjungtive Continous Glucose Monitoring Use", European Endo-crinology, 2016, vol. 12, No. 1, pp. 24-30.
Dungan et al., "Glucose Measurement: Confounding Issues in Setting Targets for Inpatient Management", Diabetes Care, Feb. 2007, vol. 30, No. 2, pp. 403-409.
Wong et al., "The introduction of insulin in type 2 diabetes mellitus", Aust. Fam. Physician, May 2015, vol. 44, No. 5, pp. 278-283.
Stumvoll et al., "Use of the Oral Glucose Tolerance Test to Assess Insulin Release and Insulin sensitivity", Diabetes Care, Mar. 2000, vol. 23, No. 3, pp. 295-301.
Jiaping et al., "Application of Mathematical Models in the Diagnosis and Prediction of Diabetes", Journal of Mathematical Medicine, Nov. 2016, vol. 29, No. 11, pp. 1581-1583.

* cited by examiner

INSULIN TITRATION ALGORITHM BASED ON PATIENT PROFILE

CROSS-REFERENCE TO RELATED APPLICATIONS

This application is a 35 U.S.C. § 371 National Stage application of International Application PCT/EP2018/065845 (published as WO 2018/229209), filed Jun. 14, 2018, which claims priority to European Patent Application 17178877.1, filed Jun. 29, 2017, this application further claims priority under 35 U.S.C. § 119 of U.S. Provisional Applications 62/520,139, filed Jun. 15, 2017 and 62/522,811, filed Jun. 21, 2017, the contents of all above-named applications are incorporated herein by reference.

FIELD OF THE INVENTION

The present disclosure relates generally to a device, system and method for assisting patients in managing pen based insulin treatment for diabetes, in which insulin injection doses are adapted to predicted risk of hypoglycemia (or hyperglycemia), the prediction being based on learning by machine learning the individuality of a patient and her/his profile as to historic blood glucose levels and injected insulin doses.

BACKGROUND OF THE INVENTION

In healthy individuals, basal insulin secretion by pancreatic β cells occurs continuously to maintain steady blood glucose (BG) levels for extended periods between meals. Also in healthy individuals, there is prandial secretion in which insulin is rapidly released in an initial first-phase spike in response to a meal, followed by prolonged insulin secretion that returns to basal levels after 2-3 hours.

Insulin is a hormone that binds to insulin receptors to lower BG level by facilitating cellular uptake of glucose, amino acids, and fatty acids into skeletal muscle and fat and by inhibiting the output of glucose from the liver. In normal healthy individuals, physiologic insulin secretions maintain normoglycemia, which affects fasting plasma glucose and postprandial plasma glucose concentrations. The insulin secretion is impaired in Type 2 diabetes and early post-meal response is absent. For patients with Type 1 diabetes there is very low to no insulin secretion at all.

Patients are usually provided with insulin medicament treatment regimens and the goal of these regimens is to maintain a desired fasting or prandial BG target level. These insulin medicament treatment regimens are based on titration algorithms that provide dose recommendations to the patients, the algorithms being based on retrospective use of historical blood glucose data, either self-monitored (SMPG) or Continuous Glucose Measuring (CGM) data, to calculate the dose recommendations. Titration algorithms are often based on ADA (American Diabetes Association) Standards of care recommendations. Patients are often under titrated due to fear of low BG levels (hypoglycemic events).

One example of such titration algorithm is a 2-0-2 titration algorithm that recommends the patient to increase the dose by 2 units, if the fasting blood glucose level is too high, or continue with the same dose dosage as previous, if the fasting blood glucose level is at normal level, or decrease the dose size by 2 units, if the fasting blood glucose level is too low.

These titration algorithms result normally in a reasonably good result however the dose recommendations are only based on the previous BG measurement data, i.e. acts only retrospectively and cannot predict future events. As long as the patient follows the same daily pattern, e.g. time of injecting the basal and/or bolus insulin, amount of insulin injected, time and amount of food intake, time and amount of exercising etc., a standard titration algorithm may give a good result with few BG fluctuations, but that's often not the case. Patients often have changes in normal routine on selected days during the week. There are many different examples for that, e.g. they have a proper meal with low carbohydrates level or they are doing sports after the meal. These types of changes may lead to changes in BG level, if the patient doesn't adjust bolus injections, which may lead to risk of hypoglycemic events. The BG level will fluctuate up and down every time an adjustment after a hypoglycemic event is made. Furthermore, the patient has to recover from the hypoglycemic event, which is very unfortunate.

In diabetes insulin treatment where both basal and bolus (prandial) insulin are taken daily (MDI, Multiple Daily Injection) using an injection pen, the risk of hypoglycemic events is usually reasonably high. Patients may use CGM to monitor BG values but studies have shown that many in particular Type 2 patients are not certain how to adjust their insulin doses based on pre-meal BG values or Rate of Change (ROC) and as a result they either skip bolus injections if the BG values are low or ROC is lower than approximately −2 mg/dl per minute. If their ROC is higher than +2 mg/dl per minute or BG values are high they increase the insulin dose to numbers that can lead to hypoglycemic events. These adjustments may result in unnecessary fluctuations in BG levels and may lead to worse adherence and long term complications for the patients, which is very unfortunate. Besides this many patients usually don't track these events and thus don't ask for advices from health care professionals. (HCP). Due to this it is important to help by calculating all possible risks associated with a given advice for bolus as well as for basal insulin injections. However, for patients using CGM and being on pen based multi-daily injections, there exists no common practice in titrating and the algorithms are based on BGM, while Post prandial blood glucose is not measured at all.

Thus, in order to help patients being on pen based MDI treatment to identify correct dose it would be preferable to have titration systems/methods that is able to predict a risk of hypoglycemic event and provide an insulin dose that will keep the patient at the normoglycemia level. It will reduce the nos. of hypoglycemic events significantly and result a less fluctuations in BG level.

Systems and methods for predicting hypoglycemic events have been described.

US 2015/0190098 disclose an adaptive advisory control interactive process involving algorithm based assessment and communication of physiologic and behavioural parameters and patterns assisting diabetics optimising their glycemic control. It provides an algorithm to retroactively compute a risk-based insulation attenuation factor to the subject's record of insulin delivery.

US 2014/0350369 discloses a system and method that provides a glucose report for determining glycemic risk based on an ambulatory glucose profile of glucose data over a time period, a glucose control assessment based on median and variability of glucose, and indicators of high glucose variability. It uses statistical methods to provide titration guidance such that glucose targets are reached in less time, with less likelihood of hypoglycaemia.

U.S. Pat. No. 8,562,587 discloses CGM-Based Prevention of hypoglycaemia System (CPHS) that may utilize CGM data to continually assess the risk of hypoglycaemia for the patient and then provides two outputs: (I) an attenuation factor to be applied to the insulin rate command sent to the pump either via conventional therapy or via open or closed loop control) and/or (2) a red/yellow/green light hypoglycaemia alarm providing to the patient an indication of the risk of hypoglycaemia.

U.S. Pat. No. 6,923,763 and US 2017/0068790 also disclose systems and methods for predicting hypoglycemia.

WO2011/157402 discloses methods and systems for diabetic patients to optimize their administered insulin dosage.

None of the above references addresses the problem of providing an insulin titration system for patients being on pen based injections that can predict hypoglycemic events and automatically adjust a first calculated insulin dose size that would result in a hypoglycemic event down to a lower second dose size in order to prevent a hypoglycemic event and communicating this to the user, this happening without any interaction with the user.

SUMMARY OF THE INVENTION

The present disclosures addresses the need in the art for devices, systems and methods for providing improved insulin titration algorithm for pen based insulin treatment and resulting in fewer fluctuations in the patients BG levels and minimizes the risk of a hypoglycemic events. More particular, the invention provides a device, system and method improving insulin titration by adding a risk predictor module to a standard basal and bolus titration algorithms. The risk predictor can predict a risk of hypoglycemia based on learning the patient's individual treatment pattern and thereby take into account future periodic deviations, where the blood glucose level is low (or high), and provide a corrected insulin dose to prevent a hypoglycemic event.

Accordingly, a first aspect of the present disclosure provides device for predicting risk of hypoglycemia and adjusting an insulin medicament dose size for a subject accordingly to prevent a predicted hypoglycemic event. The device comprises one or more processors and a memory, the memory storing a data structure comprising a prescribed insulin medicament dosage regimen that specifies a first rule based titration algorithm for computing and recommending a first dose size as an adjustment to a current dosage regimen based upon a first data set. The first data set comprises a plurality of blood glucose (BG) measurements taken over a time course, and for each respective measurement in the plurality of measurements, a corresponding timestamp representing when in the time course the respective measurement was made. The first data set further comprises a plurality of injected insulin dose size taken over a time course, and for each respective injected dose size in the plurality of injected doses, a corresponding timestamp representing when in the time course the respective dose was injected and a respective typestamp of the insulin medicament injected. The first data set comprises also a minimum target fasting and post prandial blood glucose level (mg/dl) and a maximum target for fasting and post prandial blood glucose level (mg/dl).

The data structure further comprises a risk prediction module adapted to predict risk of hypoglycemia and specifying the following machine learning algorithm modules; i) a short term risk prediction classification machine learning algorithm using a Gaussian Kernel and regularization to compute, based upon the last up to 3 hours of BG measurements from said first data set, the probability of hypoglycaemia occurring within a time period of up to 3 hours from start of computing the risk, ii) a long term risk prediction classification machine learning algorithm using a Gaussian Kernel and regularization to compute, based upon the last up to 24 hours of BG data from said first data set, the probability of hypoglycaemia occurring within a time period of up to 24 hours from start of computing the risk, iii) a subject's pattern recognition machine learning algorithm to analyse correlations between said BG measurements and insulin dose size data of said first data set and identify historic hyper- and hypoglycemic events over a predetermined period of time and the severity as to blood glucose level of each of these events.

The memory further stores instructions that, when executed by the one or more processors, perform a method comprising:
responsive to a request from the subject to compute a recommended dose for a basal or bolus insulin;
a) updating the first data set with latest available data,
b) computing a post prandial blood glucose level (PPGL) (for bolus insulin dose request) as the lowest weighted average of at least the last three days post prandial blood glucose values in the first set of data,
c) computing a titration blood glucose level (TGL) (for basal insulin dose request) as lowest weighted average of at least the last three days daily blood glucose values in the first set of data, exclusive blood glucose values identified in post prandial periods,
d) computing a first dose size by running the first rule based titration algorithm, and where the first rule based titration algorithm compute and recommend a first dose size as follows;
a first dose size being larger compared to said current dosage regimen for the subject, if said computed TGL or PPGL is above said maximum targets for fasting or post prandial blood glucose levels, or
a first dose size being decreased compared to the current dosage regimen for the subject, if said TGL or PPGL is below the said minimum targets for fasting or post prandial blood glucose levels, or
a first dose size being equal to the current dosage regimen for the subject if said average TGL or PPGL is within the range between said the minimum and maximum targets for fasting or post prandial blood glucose levels,
e) employing said short term risk prediction machine learning classification algorithm
f) employing said long term risk prediction machine learning classification algorithm
g) employing said subject's pattern recognition algorithm,
h) employing a multiple linear regression machine learning algorithm to predict a second dose size resulting in a non-hypoglycemic state for the subject based on the input from the first algorithm, the short term risk prediction algorithm, the long term risk prediction algorithm and subject's pattern recognition algorithm and if said calculated second dose size is lower than the first dose size then;
i) automatically adjusting the first dose size down to the second dose size and communicate said second dose size to the subject.

The multiple linear regression machine learning algorithm is defined by the function $$h_\theta(x) = \theta_0 + \theta_1 x^{(1)} + \theta_2 x^{(2)} + \ldots + \theta_n x^{(n)}$$

where $\theta_i$ are calculated weights corresponding to each input parameter x in determination of said second dose size h$\theta$(x) and $x^{(i)}$ are output values of the algorithms according to steps e)-g).

The step of employing said short term risk prediction machine learning classification algorithm comprises preparing from the first data set specific data sets of historic BG measurements obtained within specific time intervals of the last 15 to 180 minutes, and running each prepared data set through a support vector machine classifier with Gaussian Kernel and regularization to compute said output $x^{(i)}$ indicating risk of hypoglycemia within a future time horizon of between 15 to 180 minutes, respectively.

Said specific time intervals can be any time intervals within the 15 to 180 minutes, such as the last 15 minutes, 17 minutes, 20 minutes, 30 minutes, 35 minutes, 45 minutes, 60 minutes or more, such as 120 minutes 135 minutes or more, and the future time horizon can be any future time horizon such as 15 minutes, 17 minutes, 20 minutes, 30 minutes, 35 minutes, 45 minutes, 60 minutes or more, such as 120 minutes 135 minutes or more.

The step of employing said long term risk prediction machine learning classification algorithm comprises preparing from the first data set data sets of historic BG measurements obtained within specific time intervals of the last 12 to 24 hours, and running each prepared data set through a support vector machine classifier with Gaussian Kernel and regularization to compute said output $x^{(i)}$ indicating risk of hypoglycemia within a future time horizon of between 12 to 24 hours, respectively.

Said specific time intervals for the long term risk prediction algorithm can be any time intervals within the last 12 to 24 hours, such as the last 12.5 hours, 14 hours, 15 hours, 16 hours, 17 hours, 18.5 hours, 21 hours or more, and the future time horizon can also be any future time horizon such as 12 to 24 hours, such as the last 12.5 hours, 14 hours, 15 hours, 16 hours, 17 hours, 18.5 hours, 21 hours or more, up to 24 hours.

The step of employing said subject's pattern recognition algorithm comprises preparing from the first data set data sets of historic BG measurements obtained within specific time intervals of the last 15-180 minutes, and running each prepared data set through an single class support vector machine classifier algorithm to analyse correlations between said BG measurements of said data sets and corresponding insulin dose size data of said data sets and identify hyper- and hypoglycemic events within said time interval and the severity as to blood glucose level of each of these events. Said specific time intervals can be any intervals within the 15 to 180 minutes, such as the last 15 minutes, 17 minutes, 20 minutes, 30 minutes, 35 minutes, 45 minutes, 60 minutes or more, such as 120 minutes 135 minutes or more.

The device according to the invention provides an improved titration algorithm, where the risk prediction module is able to predict if a dose size of insulin, as recommended according the first rule based titration algorithm, will result in hypoglycemic (or hyperglycemic) event, calculate a safer second dose size and adjust the first dose size down to the second safer dose size. By this titration algorithm the patient will have much fewer fluctuations in BG level and the risk of hypos are reduced significantly.

The first rule based titration algorithm can be any titration algorithm suitable for the given treatment regimen for the patient. Examples of algorithms are shown in the below tables:

TABLE 1

Basal titration algorithm (2-0-2)

| Fasting blood glucose (TGL) | | Dose adjustment |
|---|---|---|
| mmol/L | mg/dL | |
| <4.0 | <71 | −2 U |
| 4.0-5.0 | 71-90 | No change |
| >5.0 | >90 | +2 U |

TABLE 2

Stepwise basal titration algorithm

| Fasting blood glucose (TGL) | | Dose adjustment |
|---|---|---|
| mmol/L | mg/dL | |
| <3.1 | <56 | −4 U |
| 3.1-3.9 | 56-70 | −2 U |
| 4.0-5.0 | 71-90 | No change |
| 5.1-7.0 | 91-126 | +2 U |
| 7.1-8.0 | 127-144 | +4 U |
| 8.1-9.0 | 145-162 | +6 U |
| >9.0 | >162 | +8 U |

TABLE 3

Bolus titration algorithm for adult Type 2 patients

| mmol/L | mg/dL | Dose adjustment | Frequency rule |
|---|---|---|---|
| <4.0 | <71 | −1 U | ≥1 SMPG (Self Monitored Plasma Glucose) below target |
| 4.0-6.0 | 71-108 | 0 | 0-1 SMPG above target 0 SMPG below target |
| >6.0 | >108 | +1 U | ≥2 SMPG above target 0 SMPG below target |

The risk prediction module may either calculate a complete new second dose size or it may optionally calculate a correction value to the first dose size. As an example, if the first dose size is computed to 20 units of insulin and the actual safer dose size of 15 units, the output from the risk prediction module could either be the 15 units dose size as a new dose or be a correction value of 5 units to the computed first dose of 20 units.

In some embodiments, the prescribed insulin medicament regimen includes a long acting basal insulin medicament dosage regimen, wherein the first rule based titration algorithm is adapted to compute a first dose size for the basal insulin medicament dosage and the risk prediction module is adapted compute a second dose size for the basal insulin resulting in a non-hypoglycemia state for the subject. Said dosage regimen may consist of a single insulin medicament having duration of action that is between 12 and 24 hours or a mixture of insulin medicaments that collectively have duration of action that is between 12 and 24 hours. Examples of such long acting insulin medicaments include, but are not limited to Insulin Degludec (developed by NOVO NORDISK under the brand name Tresiba).

In some embodiments, the prescribed insulin regimen also includes a short acting bolus insulin medicament dosage regimen, wherein the first algorithm is adapted to compute a first dose size for the bolus insulin medicament dosage and the risk prediction module is adapted to compute a second dose size for the bolus insulin resulting in a non-hypoglycemia state for the subject. Said dosage regimen may comprise a single insulin medicament having a duration of action that is between three to eight hours or a mixture of insulin medicaments that collectively have a duration of action that is between three to eight hours. Examples of such short acting insulin medicaments include, but are not limited, to Lispro (HUMALOG, insulin lispro [rDNA origin] injection, Eli Lilly and Company) and Aspart (NOVOLOG, insulin aspart [rDNA origin] injection, NOVO NORDISK Inc).

The short term risk prediction algorithm may use at least the previous three days of historic BG data from said first data set, but it could use more, such as the last four, five or even seven days or more. The more data available the more precise the prediction is, but the data used may be less than the previous three days, e.g. only the last two days or last one day or even less, such as last 12 hours or last 6 hours or last 4 hours. The machine learning model is preferably a support vector machine classifier, but alternatively is could be based upon ARIMA (Autoregressive Integrated Moving Average), K-NN (K-Nearest Neighbors methodology) methodology or another suitable methodology.

The long term risk prediction algorithm may use up to the previous three days of historic from said first data set, however it could be more such as previous four, five, six, seven or more days. The more data available the more precise the prediction is, but the data used may be less than previous three days, e.g. only the last two days. It is preferably based upon support vector machine classifier, but alternatively it could be based on RF (Random Forest) and/or K-NN (K-Nearest Neighbors methodology) or another suitable methodology.

The machine learning methodologies is preferably based on classification but could also be based on regression analysis depending on what fits best for the short term and long term risk prediction.

The first data set may comprise data about all previous first doses computed by the first algorithm, second doses computed by the risk prediction module and timestamps for the time of requesting dose recommendations.

In some embodiments, a second data set may be obtained comprising sets of historic data containing one or more of insulin sensitivity factor (ISF) estimations, Insulin on board (IoB) estimations, carbohydrates on board (CoB) estimations, and for each of the respective measurements a corresponding timestamp representing when in the time course the respective measurement.

The method of calculating a second dose size consists of a training stage and a prediction stage. During the training stage coefficients ($\theta_i$) are identified indicating how much influence each the individual algorithm modules of the risk prediction module impacts a dose reduction. These coefficients will be used to calculate a second dose size. The steps to identify coefficients (weights) include defining an effect factor Z being indicative of the effect the injected insulin doses from the first data set had on the blood glucose level of the subject. Z depends on the target set for the various BG levels and an example of such targets is shown in the table below. These targets are usually set by the patient's HCP and are included in the first set of data (minimum target fasting BG level (FGL2), minimum post prandial BG level (PPL2), a maximum target fasting BG level (FGH), a maximum post prandial BG level (PPH), and a hypoglycemic blood glucose alert level (FGL1/PPL1). Examples of dose guidance ranges showing how effect factor Z can be indicative of the effect the injected insulin doses from the first data set had on the blood glucose level of the subject can be found in FIG. 5.

The following is an example of how Z is defined:
the dose should not be changed (Z=0) if the injection hasn't led to a hypoglycaemic event, e.g. if the post prandial glucose level (PPBG) is above PPL2 (80 mg/dl) or the fasting blood glucose level (FBG) is above FGL2 (80 mg/dl), the dose should be lowered by titration step, e.g. 1 unit of bolus insulin or 2 units of basal insulin, (Z=−1 or −2) if the BG level is staying for one hour between PPL1 and PPL2 (bolus) or between FGL1 and FGL2 (basal), and the dose should be lowered by 20% to prevent a hypoglycemic event, if the BG level is staying lower than PPL1 or FGL1.

The method then continues with calculating safe doses Y that result in a non-hypoglycaemic state for the subject, said safe doses Y being defined as the difference between the injected amount of insulin in units and the Z value, for example Y=20 units (historic injected insulin dose)−2 (Z)=18.

The method then continues with building a machine learning hypothesis function $h_\theta$ based on input from the subject's pattern recognition algorithm, short term risk prediction algorithm and long term risk prediction algorithm, $$h_{\theta_i} = \theta_0 + \theta_1 x^{(1)} + \theta_2 x^{(2)} + \ldots + \theta_n x^{(n)} \qquad (1)$$

where $\theta_i$ are calculated coefficients and x is inputs from the algorithms.

The method then continues with defining actual number of units said first dose size should be lowered to prevent a predicted hypoglycemic event, the actual number being calculated based on minimization model (squared error function):

$$\min_\theta \frac{1}{2m} \sum_{i=1}^{m} (h_\theta(x^{(i)}) - y^{(i)})^2$$

where x is the input from the subject's pattern recognition algorithm, short term risk prediction algorithm and long term risk prediction algorithm, y is the safe dose sizes, and m is number of individual insulin injections.

The set of values $\theta_i$ is used in a prediction stage to calculate the second dose size using the formula (1) above.

The device preferably comprises a wireless receiver, and wherein the blood glucose measurements of the first data set is obtained wirelessly from a CGM affixed to the subject and the insulin dose data of the first data set is obtained wirelessly from one or more insulin pens adapted to communicate with the wireless receiver. The pen may either be a durable or a disposable injection pen. Self-monitored blood glucose (SMPG) measurements (finger prick) could theoretically also be used but practically SMPG measurements are most often not taken frequently enough by the patients (usually only 1-2 times per day), which doesn't give sufficient data for a proper prediction calculation.

In some embodiments, the successive measurements in the plurality of glucose measurements may be taken autonomously by the CGM device from the subject at an interval rate of 15 minutes or less, 3 minutes or less, or 1 minute or less.

In some embodiments, the data structure further comprises a data set of historic data about the subject's historic geographical positions, cardiovascular activity, food intake, calendar events, heart rate, skin temperature, skin impedance and/or respiration, for each of the respective measurements a corresponding timestamp representing when in the time course the respective measurement was made. This data set being used by the risk prediction module to predict a risk of hypoglycaemia.

A second aspect of the invention provides a system for assisting a subject in treating diabetes and comprising a device according to the first aspect integrated into an application running on a mobile device, such as a mobile phone, laptop or tablet, said application being adapted to at least communicate on said mobile device the first and second dose size recommendations to the subject. In some embodiments, the BG data and insulin injection data for the first data set is wirelessly communicated directly from the CGM and injection pen(s) to the mobile device. The mobile device could be a smart phone or a tablet.

A third aspect of the invention provides method for assisting a subject in treating diabetes via a computer system comprising one or more processors and a memory storing a data structure comprising;
- a prescribed insulin medicament dosage regimen that specifies a first rule based titration algorithm for computing and recommending a first dose size as an adjustment to a current dosage regimen based upon a first data set comprising:
  - a plurality of blood glucose (BG) measurements taken over a time course, and for each respective measurement in the plurality of measurements, a corresponding timestamp representing when in the time course the respective measurement was made,
  - a plurality of injected insulin dose size taken over a time course, and for each respective injected dose size in the plurality of injected doses, a corresponding timestamp representing when in the time course the respective dose was injected and a respective typestamp of the insulin medicament injected,
  - minimum target fasting and post prandial blood glucose levels,
  - maximum target fasting and post prandial blood glucose levels,
- a risk prediction module comprising the following machine learning algorithm modules:
  - a short term risk prediction classification machine learning algorithm using an activation function to compute, based upon the last up to 3 hours of BG measurements from said first data set, the probability of hypoglycaemia occurring within a time period of up to 3 hours from start of computing the risk,
  - a long term risk prediction classification machine learning algorithm using an activation function to compute, based upon the last up to 24 hours of BG data from said first data set, the probability of hypoglycaemia occurring within a time period of up to 24 hours from start of computing the risk,
  - a subject's pattern recognition machine learning algorithm to analyse correlations between said BG measurements and insulin dose size data of said first data set and identify historic hyper- and hypoglycemic events over a predetermined period of time and the severity as to blood glucose level of each of these events,
wherein the memory further stores instructions that, when executed by the one or more processors, perform a method comprising:
responsive to a request from the subject to compute a recommended dose for a basal or bolus insulin;
a) updating the first data set with latest available data,
b) computing a post prandial blood glucose level (PPGL) (for bolus insulin dose request) as the lowest weighted average of at least the last three days post prandial blood glucose values in the first set of data,
c) computing a titration blood glucose level (TGL) (for basal insulin dose request) as lowest weighted average of at least the last three days daily blood glucose values in the first set of data, exclusive blood glucose values identified in post prandial periods,
d) computing a first dose size by running the first rule based titration algorithm, and where the first rule based titration algorithm compute and recommend a first dose size as follows;
  - a first dose size being larger compared to said current dosage regimen for the subject, if said computed TGL or PPGL is above said maximum targets for fasting or post prandial blood glucose levels, or
  - a first dose size being decreased compared to the current dosage regimen for the subject, if said TGL or PPGL is below the said minimum targets for fasting or post prandial blood glucose levels, or
  - a first dose size being equal to the current dosage regimen for the subject if said average TGL or PPGL is within the range between said the minimum and maximum targets for fasting or post prandial blood glucose levels,
e) employing said short term risk prediction machine learning classification algorithm
f) employing said long term risk prediction machine learning classification algorithm
g) employing said subject's pattern recognition algorithm,
h) employing a multiple linear regression machine learning algorithm to predict a second dose size resulting in a non-hypoglycemic state for the subject based on the input from the first algorithm, the short term risk prediction algorithm, the long term risk prediction algorithm and subject's pattern recognition algorithm and if said calculated second dose size is lower than the first dose size then;
i) automatically adjusting the first dose size down to the second dose size and communicate said second dose size to the subject.

The multiple linear regression machine learning algorithm is defined by the function $$h_\theta(x)=\theta_0+\theta_1 x^{(1)}+\theta_2 x^{(2)}+ \ldots +\theta_i x^{(n)}$$

where $\theta_i$ are calculated weights corresponding to each input parameter x in determination of said second dose size $h_\theta(x)$ and $x^{(i)}$ are output values of the algorithms according to steps e)-g).

The step of employing said short term risk prediction machine learning classification algorithm comprises preparing from the first data set specific data sets of historic BG measurements obtained within specific time intervals of the last 15 to 180 minutes, and running each prepared data set through a support vector machine classifier with Gaussian Kernel and regularization to compute said output $x^{(i)}$ indicating risk of hypoglycemia within a future time horizon of between 15 to 180 minutes, respectively. Said specific time intervals can be any time intervals within the 15 to 180 minutes, such as the last 15 minutes, 17 minutes, 20 minutes, 30 minutes, 35 minutes, 45 minutes, 60 minutes or more, such as 120 minutes 135 minutes or more, and the future time horizon can be any future time horizon such as 15 minutes, 17 minutes, 20 minutes, 30 minutes, 35 minutes, 45 minutes, 60 minutes or more, such as 120 minutes 135 minutes or more.

The step of employing said long term risk prediction machine learning classification algorithm comprises preparing from the first data set data sets of historic BG measurements obtained within specific time intervals of the last 12 to 24 hours, and running each prepared data set through a support vector machine classifier with Gaussian Kernel and regularization to compute said output $x^{(i)}$ indicating risk of hypoglycemia within a future time horizon of between 12 to 24 hours, respectively. Said specific time intervals for the long term risk prediction algorithm can be any time intervals within the 12 to 24 hours, such as the last 12.5 hours, 14 hours, 15 hours, 16 hours, 17 hours, 18.5 hours, 21 hours or more, and the future time horizon can also be any future time horizon such as 12 to 24 hours, such as the last 12.5 hours, 14 hours, 15 hours, 16 hours, 17 hours, 18.5 hours, 21 hours or more, up to 24 hours.

The step of employing said subject's pattern recognition algorithm comprises preparing from the first data set data sets of historic BG measurements obtained within specific time intervals of the last 15-180 minutes, and running each prepared data set through an single class SVM classifier algorithm to analyse correlations between said BG measurements of said data sets and corresponding insulin dose size data of said data sets and identify hyper- and hypoglycemic events within said time interval and the severity as to blood glucose level of each of these events. Said specific time intervals can be any time intervals within the 15 to 180 minutes, such as the last 15 minutes, 17 minutes, 20 minutes, 30 minutes, 35 minutes, 45 minutes, 60 minutes or more, such as 120 minutes 135 minutes or more.

By the invention as described above each patient is risk-stratified in real time based on each patient's first set of data (also called "Patient's metric"). A machine learning model assesses the BG measurements and produces predictive hypoglycemic warnings at e.g. 24 hours, 15 hours, 12 hours, 3 hours, 2 hours, 60 minutes, 30 minutes or 15 minutes prediction horizons. The hypoglycemic warnings may be communicated to the patient, e.g. via an application on a mobile phone, following rules dictated by the patient's risk profile. In some embodiments, the device is accessible within any browser (phone, tablet, laptop/desktop).

All data used by the device to predict the risk of hypoglycemia may be accessible via a mobile device, server or cloud.

The device, system and method according to the invention builds on a machine learning approach to learn the individual patient's pattern and behavior in terms of historic BG levels and insulin injections. The invention can automatically adjust a given recommended insulin dosage, computed from a standard titration algorithm, to a lower safer dose size in case low BG values are predicted on a specific day and/or specific time of day. It means that the standard titration algorithm (first algorithm) will not fall into a loop of recovering from the occasional hypoglycemic events, as the risk prediction module will foresee these events before they happen and correct the dose. This will reduce number of hypoglycemic events meaning less long term complications and result in better adherence for the patient.

It should be understood that the device and method according to the invention also is able to predict a risk of hyperglycemia (high BG levels) and adjust a first recommended insulin dose size to a second recommended dose size, in this case a second dose size being higher than the first dose size in order to reduce the BG level and prevent a hyperglycemic event.

DETAILED DESCRIPTION

The present disclosure relies upon the acquisition of data regarding a data set comprising a plurality of glucose measurements of a subject taken over a time course and, for each respective glucose measurement in the plurality of glucose measurements, a corresponding timestamp representing when in the time course the respective glucose measurement was made, said data preferably being acquired via a continuous glucose monitoring device (CGM) worn by the subject.

The present disclosure also relies upon acquisition of data from one or more insulin pens used to apply a recommended dose of prescribed insulin to the subject. Each record comprises a timestamp also specifying an amount of injected insulin medicament and the type of insulin injected. By recording the type of insulin the device receives information regarding the specific PK/PD (Pharmacokinetics/Pharmacodynamics) profiles of the given insulin, which is used to calculate the Insulin on Board (IoB) factor in the subject, a factor that may be used in predicting BG levels.

Reference will now be made in detail to embodiments, examples of which are illustrated in the accompanying drawings. In the following detailed description, more specific details are set forth in order to provide a more thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. By the term insulin pen is meant an injection device suitable for applying discrete doses of insulin, and wherein the injection device is adapted for logging and communicating dose related data.

Figure 1:
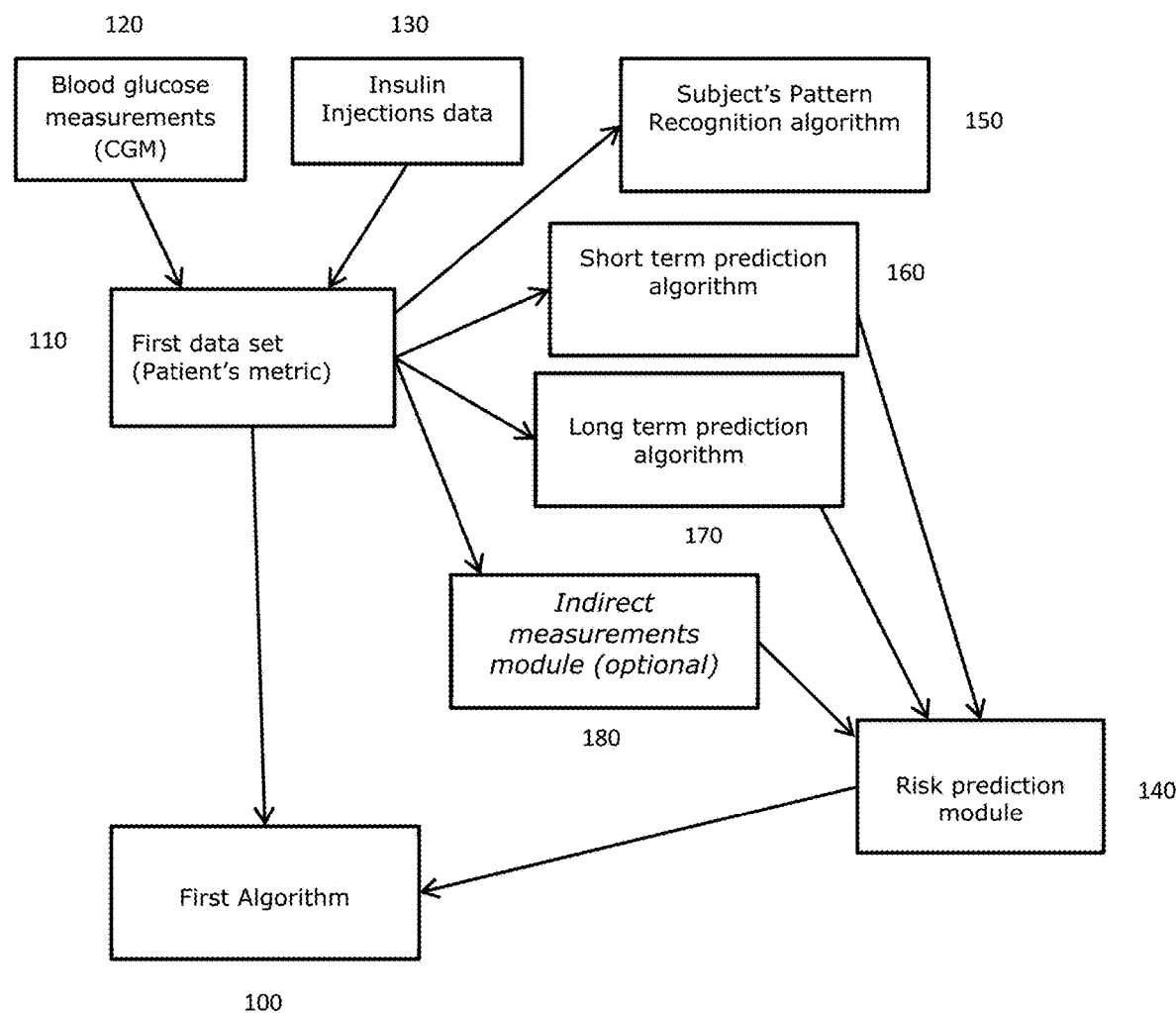
FIG. 1 illustrates an exemplary system topology of the modules included in the device for predicting risk of hypoglycemia and adjusting an insulin medicament dosage for a subject accordingly, in accordance with an embodiment of the present disclosure.

Referring to FIG. 1, an exemplary system topology of the modules included in the device and method according to the invention is shown, wherein a first algorithm 100 is adapted to compute a recommendation for a first dose size to the patient, said first algorithm computing the dose size recommendation based upon a retrospective analysis of the historic BG and insulin injection data included in the first data set 110 (Patient's Metric). The data in the first data set is fed into the device via a wireless receiver, where the BG measurements 120 is obtained wirelessly from a CGM affixed to the subject and the insulin injections data 130 is obtained wirelessly from one or more insulin pens adapted to communicate with the wireless receiver. For instance, in some embodiments the device receives this data wirelessly through radio-frequency signals. In some embodiments such signals are in accordance with an 802.11 (WiFi), Bluetooth, or ZigBee standard. In some embodiments, the CGM and/or insulin injection pen includes an RFID tag and communicates to the device. In some embodiments, the first data set also includes physiological measurements of the subject (e.g., from wearable physiological measurement devices, etc).

The glucose sensor may e.g. be a FREESTYLE LIBRE CGM by ABBOTT ("LIBRE") used to make autonomous glucose measurements of a subject. The LIBRE allows calibration-free glucose measurements with an on-skin coin-sized sensor, which can send up to eight hours of data to the device via near field communications or Bluetooth or any other suitable protocol. Another example of a glucose sensor is DEXCOM G5.

In some embodiments, the device is not proximate to the subject and/or does not have wireless capabilities or such wireless capabilities are not used for the purpose of acquiring glucose data, insulin medicament injection data, and/or physiological measurement data. In such embodiments, a communication network may be used to communicate data.

In order to predict a risk of hypoglycemia, the device comprises, in addition the first algorithm, a risk prediction module 140 that receives input from a plurality of separate algorithm modules. One such module is the subject's pattern recognition algorithm module 150 that is adapted to analyze the correlations between the BG measurement data and insulin injection data of the first data set 110 in order to identify historic hyper- and hypoglycemic events over a predetermined period of time and the severity as to BG level of each of these events.

Another module is the short term risk prediction algorithm module 160 that is able to predict a risk of hypoglycemia occurring within a time period of up to 2 hours from start of computing the risk. The risk prediction being computed based only on the BG measurements of the first data set. However, other data than the BG measurements may be used to compute the risk.

Yet another module is the long term risk prediction algorithm module 170 is able to predict a risk of hypoglycaemia occurring within a time period of up to 24 hours from start of computing the risk. The risk prediction being computed by running a machine learning classification algorithm and based only on the BG measurements of said first data set. Other data than BG measurements may be used to compute the risk.

Based on input from the above described modules, a multiple linear regression machine learning algorithm to predict a risk of hypoglycemia and calculates the second dose size being resulting in a non-hypoglycemic state. If the second dose size is lower than the dose first dose size calculated by the first algorithm, the risk prediction module communicates this new second dose size to the patient.

A further indirect measurements module 180 may be included containing sets of historic data of one or more of insulin sensitivity factor (ISF) measurements, Insulin on board (IoB) measurements, carbohydrates on board (CoB) measurements, and for each of the respective measurements a corresponding timestamp representing when in the time course the respective measurement, said second data set being used by the risk prediction module to predict a risk of hypoglycaemia. This module 180 feeds data to the risk prediction module 140 to be used in predicting the risk and calculates a corrected insulin dose resulting in a non-hypoglycaemic state for the patient.

The first data set also comprises minimum and maximum targets for BG level and it may also comprise data about the insulin to carbohydrates ratio and potentially also body weight, as depicted in module 190 in FIG. 1.

Figure 2:
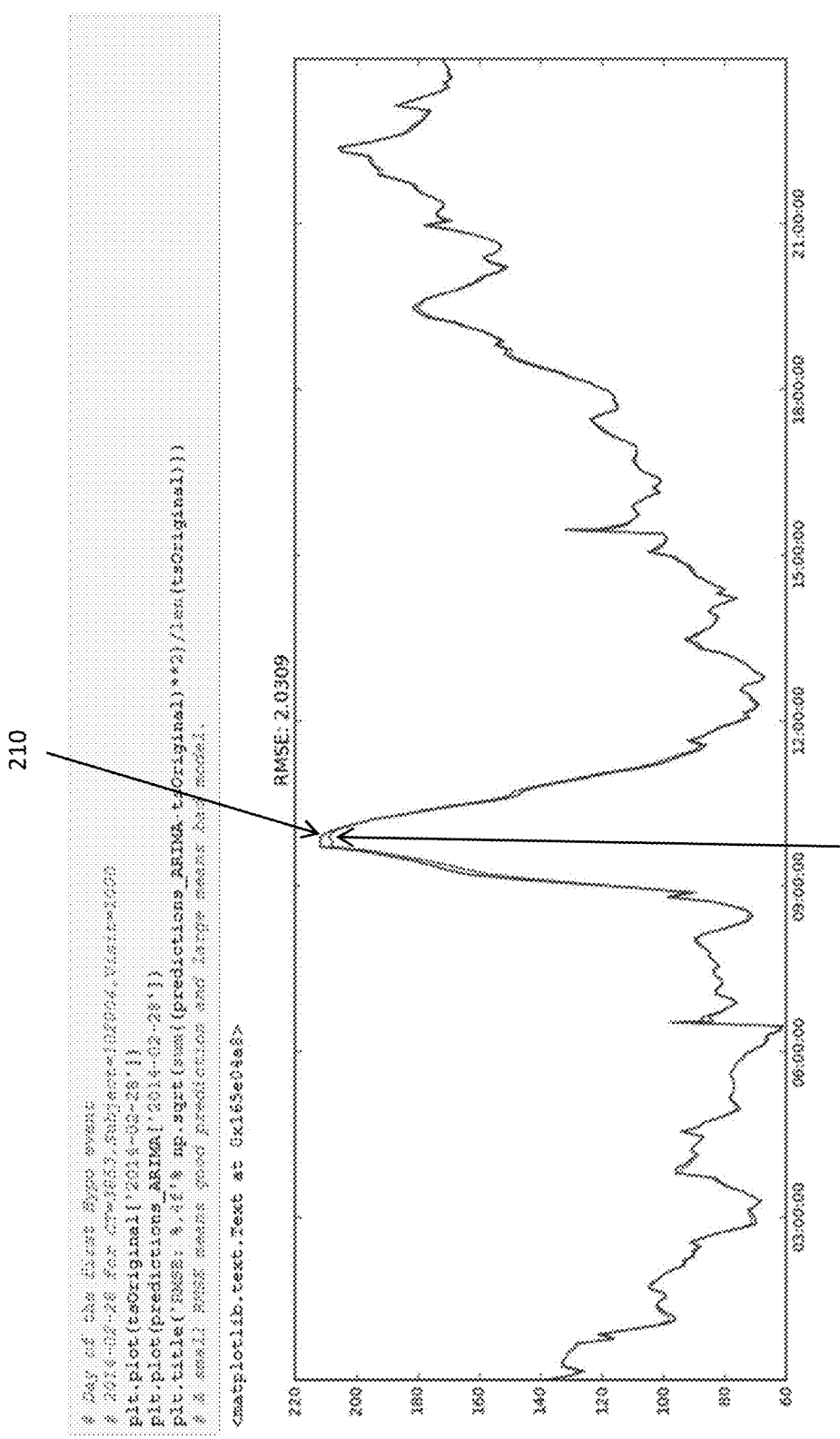
FIG. 2 shows graphs of BG levels originally measured vs. BG levels predicted by a device for predicting a risk of hypoglycemia according to the invention.

Turning to FIG. 2, a graph 200 showing BG levels originally measured in a patient is compared to a graph 210 showing BG levels predicted by the risk prediction module and with a 15 minutes risk prediction time horizon over a period of 24 hours. The prediction is based on historic BG data only, and as can be seen, the risk prediction module is able to predict the BG levels with a very high accuracy, as there is a very little difference in BG values between the two graphs. An often used value to represent the differences between predicted values and observed values model is the RMSE (Root Mean Square Error) value. The RMSE value can be considered as a performance measure for the risk prediction model, and in the example shown the RMSE value is 2.0309 mg/dl for BG values ranging from 60-220 mg/dl, which is considered a very low RMSE representing a very good performance of by the risk prediction module.

Figure 3A:
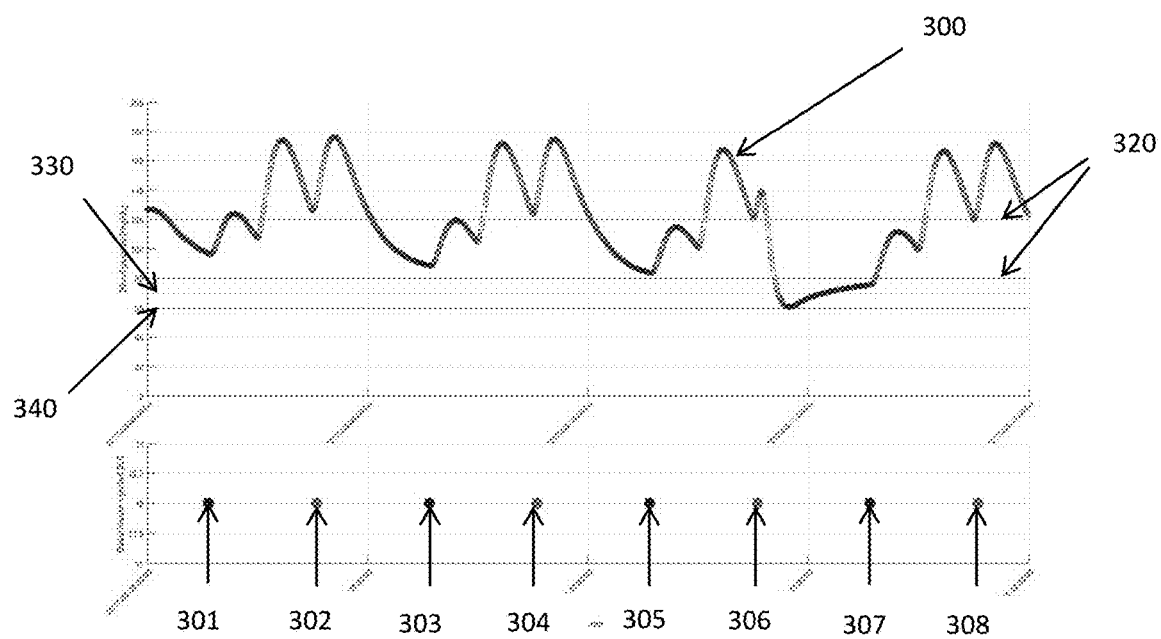
FIGS. 3*a-b* illustrate data plots of BG levels and associated injected doses of basal insulin over time for a patient taking basal insulin doses computed according to the first algorithm and computed by a device/system/method according to the invention, respectively.
Figure 3B:
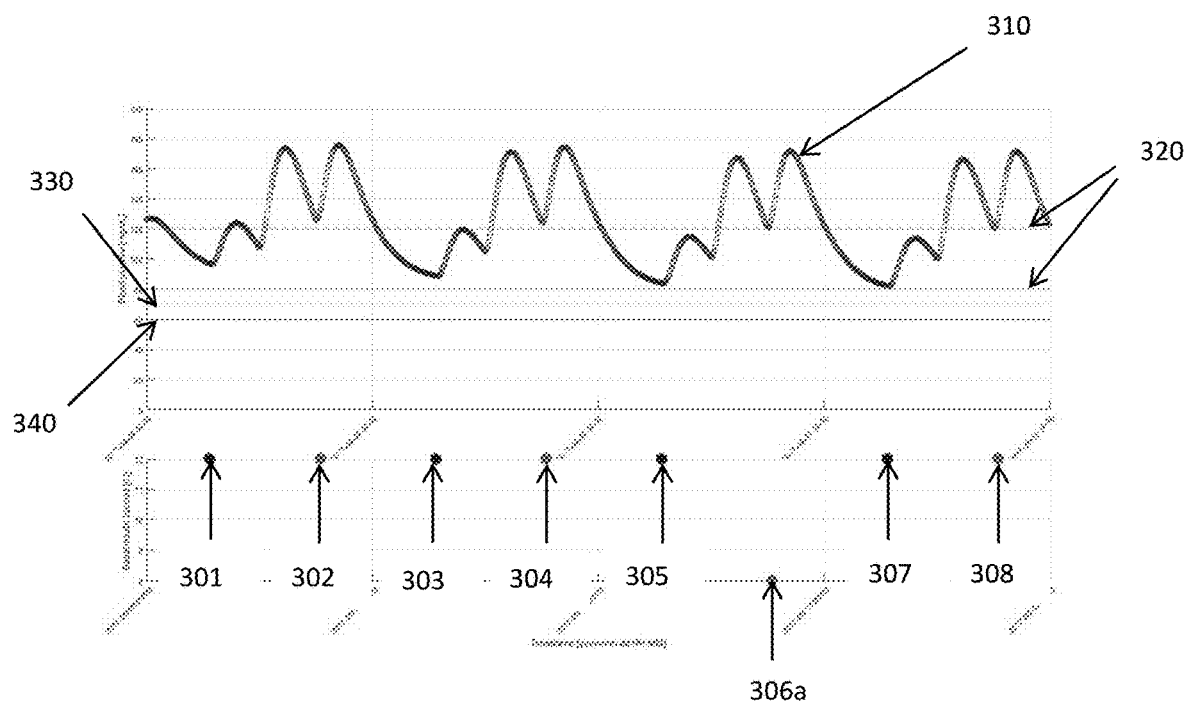

FIG. 3a illustrates a data plot of a patient's BG levels and associated injected dose sizes of basal and bolus insulin over time (horizontal axis indicates time). The curve 300 shows a patient's BG profile over time for a patient taking basal (301, 303, 305, 307) and bolus (302, 304, 306, 308) insulin doses as computed and recommended according to first algorithm. FIG. 3b shows same kind of a data plot, but where curve 310 shows a patient's BG profile over time for a patient taking basal insulin doses (301, 303, 305, 307) and bolus insulin doses (302, 304, 306a, 308) as computed and recommended by a device/system/method according to the invention. The lines 320 define the normoglycemic state with BG ranges from 80-120 mg/dl, whereas the lines 330, 340 define the hypoglycemic state with BG ranges of 70 mg/dl and 60 mg/dl, respectively.

A patient may have changes in her/his normal routine on selected days during the week. There are many reasons for that, such as having a low carb meal or doing sports after the meal. Such changes are referred to by changes in bolus injections. As can be seen in FIG. 3a, the BG level after injection of bolus dose 306 changes suddenly and gets below 70 mg/dl and the patient gets into a hypoglycemic state. The first algorithm is not able to predict such a periodic deviation, as it only acts retrospectively.

Now turning to FIG. 3b, as can be seen the drop in BG level is avoided, as the risk prediction module is able to, based on the learning of the patients pattern, predict the hypoglycemic state.

By the adding the risk prediction module to the first algorithm, a titration algorithm is provided that is able to predict hypoglycemic event AND act proactively and automatically calculate a new lower bolus dose 306a and over-rule the a recommended dose 306. Thereby, the patient will inject the second dose size 306a and not a first recommended dose size 306, whereby the BG level will not drop below 70 mg/dl (as depicted in the graph). The patient is kept in the normoglycemic range and will not suffer from a hypo and the recovering from that. The patient will have fewer fluctuations in the BG level.

Figure 4A:
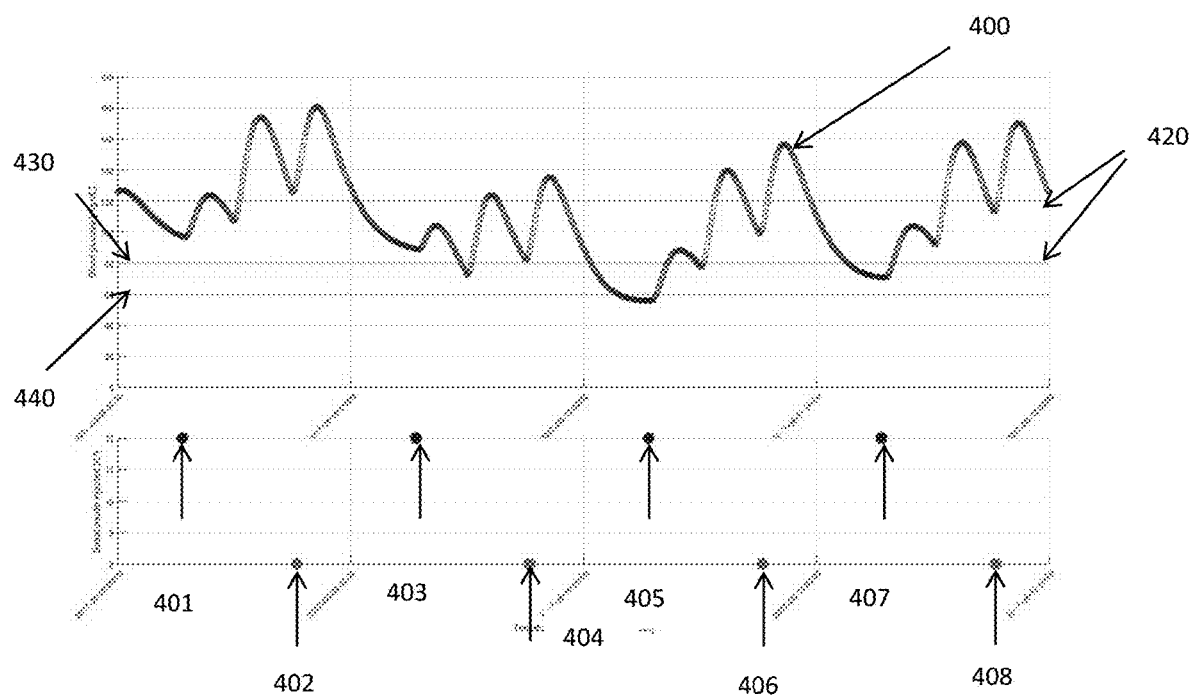
FIGS. 4*a-b* illustrate data plots of BG levels and associated injected doses of bolus insulin over time for a patient taking bolus insulin doses computed according to the first algorithm and computed by a device/system/method according to the invention, respectively.
Figure 4B:
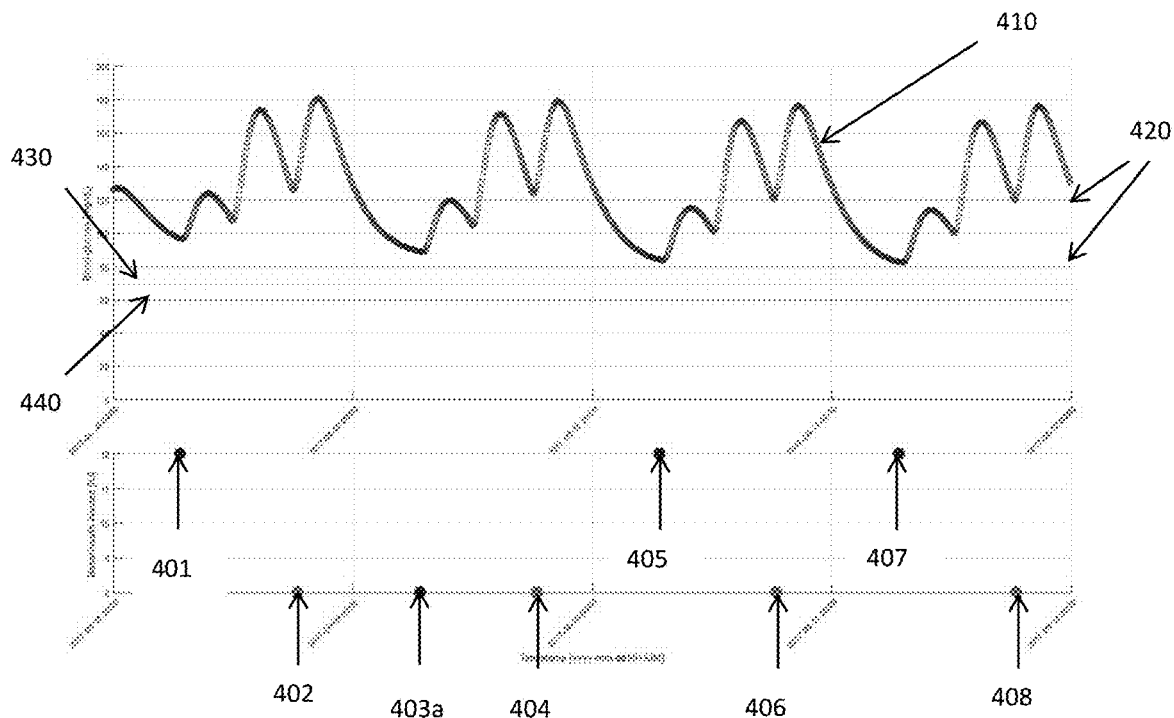
Figure 5:
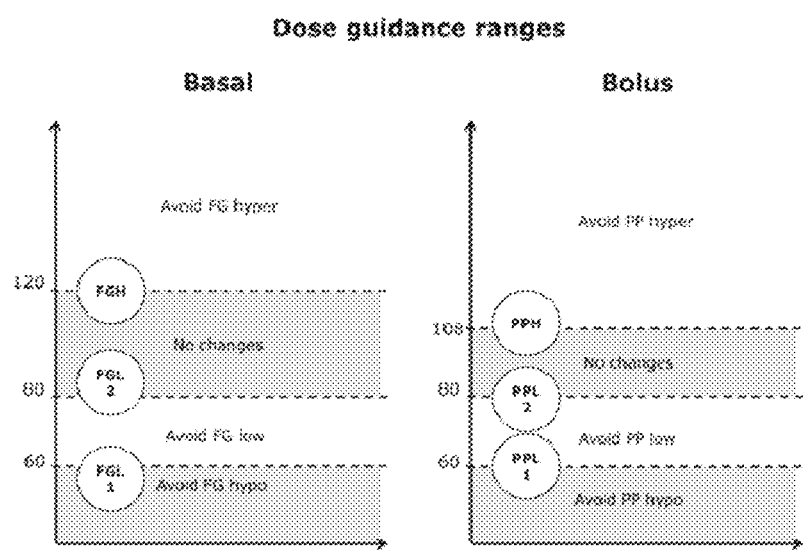
FIG. 5 illustrates dose guidance ranges showing how effect factor Z can be indicative of the effect the injected insulin doses from the first data set had on the blood glucose level of the subject.

FIGS. 4a-b illustrate the same pattern as FIGS. 3a-b, here it is just basal dose adjustment instead of bolus dose adjustment. The curve 400 shows a patient's BG profile over time for a patient taking basal (401, 403, 405, 407) and bolus (402, 404, 406, 408) doses as computed and recommended according to a standard insulin titration algorithm (referred to as the first algorithm). FIG. 4b shows same kind of a data plot, but where curve 410 shows a patient's BG profile over time for a patient taking basal insulin doses (401, 403a, 405, 407) and bolus insulin doses (402, 404, 406, 408) as computed and recommended by a device/method in according to the invention. The lines 420 define the normoglycemic state with BG ranges from 80-120 mg/dl, whereas the lines 430, 440 define the hypoglycemic state with BG ranges of 70 mg/dl and 60 mg/dl, respectively.

Again, the patient may have changes in her/his normal routine on selected days during the week. As can be seen in FIG. 4a, the patient's' fasting BG level goes below 60 mg/dl after basal injection 403 and bolus injection 404 meaning the patient just after the fasting period is in a hypoglycemic state. It may be due to the fact that the patient is having heavy physical activity or a low carb dinner meal that specific evening or a fasting day in the week. To avoid a hypoglycemic event caused by the injections of long acting basal insulin it is necessary to reduce the dose 1-2 days before then, so in this example there is obviously a need for reducing the basal insulin dose 403 in order to prevent the hypoglycemic state the next morning. However the first algorithm is not able to predict such periodic deviation proactively, as it only acts retrospectively.

Now turning to FIG. 4b and the associated insulin injections, the hypoglycemic state after basal injection dose 403 in FIG. 4a has been predicted by the risk prediction module according to the invention, i.e. the low BG level is predicted and avoided as the risk prediction module proactively and automatically calculates a new second lower basal dose 403a and inputs this dose to the first algorithm and thereby overrules the first recommended dose 403. Thereby, the patient will inject the second dose size 403a and not a first recommended dose size 403, whereby the BG level will not drop below 70 mg/dl (as depicted in the graph). The patient is kept in the normoglycemic range during fasting period.

The present invention can be implemented as a computer program product that comprises a computer program mechanism embedded in a non-transitory computer readable storage medium. For instance, the computer program product could contain the modules shown in any combination of FIG. 1. These modules can be stored on a CD-ROM, DVD, magnetic disk storage product, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the Invention and various embodiments with various modifications as are suited to the particular use contemplated. The invention is to be limited only by the terms of the appended claims, along with the full scope of equivalents to which such claims are entitled.

The invention claimed is:

1. A method for assisting a subject in treating diabetes via a computer system comprising one or more processors and a memory storing a data structure comprising;

a prescribed insulin medicament dosage regimen that specifies a first rule based titration algorithm for computing and recommending a first dose size as an adjustment to a current dosage regimen based upon a first data set comprising:

a plurality of blood glucose (BG) measurements taken over a time course, and for each respective measurement in the plurality of measurements, a corresponding timestamp representing when in the time course the respective measurement was made, a plurality of injected insulin dose size taken over a time course, and for each respective injected dose size in the plurality of injected doses, a corresponding timestamp representing when in the time course the respective dose was injected and a respective typestamp of the insulin medicament injected, minimum target fasting and post prandial blood glucose levels, maximum target fasting and post prandial blood glucose levels, a risk prediction module comprising the following machine learning algorithm modules:

a short term risk prediction classification machine learning algorithm using a Gaussian Kernel and regularization to compute, based upon the last up to 3 hours of BG measurements from said first data set, the probability of hypoglycaemia occurring within a time period of up to 3 hours from start of computing the risk, a long term risk prediction classification machine learning algorithm using a Gaussian Kernel and regularization to compute, based upon the last up to 24 hours of BG data from said first data set, the probability of hypoglycaemia occurring within a time period of up to 24 hours from start of computing the risk, a subject's pattern recognition machine learning algorithm to analyse correlations between said BG measurements and insulin dose size data of said first data set and identify historic hyper- and hypoglycemic events over a predetermined period of time and the severity as to blood glucose level of each of these events, wherein the memory further stores instructions that, when executed by the one or more processors, perform a method comprising:

responsive to a request from the subject to compute a recommended dose for a basal or bolus insulin, performing a set of steps for automatically adjusting the recommended dose without further interaction by the subject, the set of steps comprising:

a) updating the first data set with latest available data, comprising syncing with at least one of a continuous glucose measurement system (CGM) or one or more insulin pens, b) computing a post prandial blood glucose level (PPGL) (for bolus insulin dose request) as the lowest weighted average of at least the last three days post prandial blood glucose values in the first set of data, c) computing a titration blood glucose level (TGL) (for basal insulin dose request) as lowest weighted average of at least the last three days daily blood glucose values in the first set of data, exclusive blood glucose values identified in post prandial periods, d) computing a first dose size by running the first rule based titration algorithm, and where the first rule based titration algorithm compute and recommend a first dose size as follows;

a first dose size being larger compared to said current dosage regimen for the subject, if said computed TGL or PPGL is above said maximum targets for fasting or post prandial blood glucose levels, or a first dose size being decreased compared to the current dosage regimen for the subject, if said TGL or PPGL is below the said minimum targets for fasting or post prandial blood glucose levels, or a first dose size being equal to the current dosage regimen for the subject if said average TGL or PPGL is within the range between said the minimum and maximum targets for fasting or post prandial blood glucose levels, e) employing said short term risk prediction machine learning classification algorithm, comprising retrieving, from the first data set including the latest available data, short-term data including the last up to 3 hours from said first data set, determining a probability of hypoglycaemia occurring based on the short-term data, and providing at least a first output value $x^{(1)}$ based on the probability of hypoglycaemia occurring based on the short-term data, f) employing said long term risk prediction machine learning classification algorithm, comprising retrieving, from the first data set including the latest available data, long-term data including the last up to 24 hours from said first data set, determining a probability of hypoglycaemia occurring based on the long-term data, and providing at least a second output value $x^{(2)}$ based on the probability of hypoglycaemia occurring based on the long-term data, g) employing said subject's pattern recognition algorithm, comprising determining at least one correlation between the first data set including the latest available data and a historic hyperglycemic event or hypoglycemic event particularized to the subject, and providing at least a third output value $x^{(3)}$ based on a probability based on the at least one correlation, h) employing multiple linear regression machine learning algorithms to calculate a second dose size comprising a training stage algorithm and a prediction stage algorithm, wherein during the training stage, coefficients ($v_i$) are identified indicating weights corresponding to how much influence each the individual algorithm modules of the risk prediction module impacts a dose reduction, wherein the training stage coefficients ($v_i$) are used to calculate a second dose size, resulting in a non-hypoglycemic state for the subject based on the input from the first algorithm, the short term risk prediction algorithm, the long term risk prediction algorithm and subject's pattern recognition algorithm, i) automatically adjusting the first dose size down to the second dose size when said calculated second dose size is lower than the first dose size and, when automatically adjusting the first dose size, communicate the adjusted first dose size to the subject to thereby prevent a predicted hypoglycemic event, wherein the computer system is configured to communicate the adjusted first dose size to the subject at least a predetermined amount of time in advance of the predicted hypoglycemic event, said predetermined amount of time particularized to the subject, wherein the second dose size is calculated from the set of values $v_i$ used in a prediction stage algorithm of the multiple linear regression machine learning algorithm and is defined by the function:

$$h_\theta(x)=\theta_0+\theta_1 x^{(1)}+\theta_2 x^{(2)}+ \ldots +\theta_n x^{(n)}$$

where $\theta_i$ are calculated weights corresponding to each input parameter x in determination of said second dose size $h_\theta(x)$ and $x^{(i)}$ are output values of the algorithms according to steps e)-g);

administering the first dose size or the adjusted dose size to the subject.

2. A method according to claim 1, wherein the step of employing said short term risk prediction machine learning classification algorithm comprises;

preparing from the first data set specific data sets of historic BG measurements obtained within specific time intervals of the last 15 to 180 minutes, running each prepared data set through a support vector machine classifier with Gaussian Kernel and regularization to compute said output $x^{(i)}$ indicating risk of hypoglycemia within a future time horizon of between 15 to 180 minutes, respectively.

3. A method according to claim 1, wherein the step of employing said long term risk prediction machine learning classification algorithm comprises;

preparing from the first data set data sets of historic BG measurements obtained within specific time intervals of the last 12 to 24 hours, running each prepared data set through a support vector machine classifier with Gaussian Kernel and regularization to compute said output $x^{(i)}$ indicating risk of hypoglycemia within a future time horizon of between 12 to 24 hours, respectively.

4. A method according to claim 1, wherein the step of employing said subject's pattern recognition algorithm comprises;

preparing from the first data set data sets of historic BG measurements obtained within specific time intervals of the last 15-180 minutes, running each prepared data set through an single class SVM classifier algorithm to analyse correlations between said BG measurements of said data sets and corresponding insulin dose size data of said data sets and identify hyper- and hypoglycemic events within said time interval and the severity as to blood glucose level of each of these events.

* * * * *